United States Patent [19]
Schulte et al.

[11] Patent Number: 5,464,411
[45] Date of Patent: Nov. 7, 1995

[54] VACUUM-ASSISTED FIXATION APPARATUS

[75] Inventors: Reinhard W. Schulte, Colton; William J. Wicks, Redondo Beach; Helmut J. Meinass, Colton; Winston J. Nethery, Yorba Linda, all of Calif.

[73] Assignee: Loma Linda University Medical Center, Loma Linda, Calif.

[21] Appl. No.: 148,213

[22] Filed: Nov. 2, 1993

[51] Int. Cl.$^6$ .................................................. A61B 19/00
[52] U.S. Cl. ............................................................ 606/130
[58] Field of Search .......................... 128/846, 859–862; 606/1, 130, 234–236; 294/64.1, 64.3, 65; 601/23, 24, 139

[56] References Cited

U.S. PATENT DOCUMENTS

| | | |
|---|---|---|
| 1,202,971 | 10/1916 | Daiber . |
| 4,270,531 | 6/1981 | Blachly .................................. 128/861 |
| 4,550,713 | 11/1985 | Hyman .................................... 606/130 |
| 4,583,949 | 4/1986 | Heartness . |
| 4,591,341 | 5/1986 | Andrews . |
| 4,602,622 | 7/1986 | Bar et al. . |
| 4,841,965 | 6/1989 | Jacobs . |
| 4,917,344 | 4/1990 | Prechter et al. . |
| 4,971,060 | 11/1990 | Schneider et al. . |
| 5,039,057 | 8/1991 | Prechter et al. . |
| 5,090,047 | 2/1992 | Angotti et al. . |
| 5,094,241 | 3/1992 | Allen . |
| 5,107,839 | 4/1992 | Houdek et al. . |
| 5,117,829 | 6/1992 | Miller et al. . |
| 5,207,688 | 5/1993 | Carol ..................................... 606/130 |
| 5,221,283 | 6/1993 | Chang .................................... 606/130 |
| 5,230,623 | 7/1993 | Gutherie et al. . |
| 5,260,581 | 11/1993 | Lesyna et al. . |
| 5,269,305 | 12/1993 | Carol . |
| 5,281,232 | 1/1994 | Hamilton et al. . |

FOREIGN PATENT DOCUMENTS 2213066A 9/1989 United Kingdom .

OTHER PUBLICATIONS

The Laitinen Stereoadapter: Application to the fractionated stereotactic irradiation of the brain; Delannes et al., Neurochirurgie, 1990, 36:167–175. (in French and with English translation).

A Halo–ring technique for fractionated stereotactic radiotherapy; Clark et al., The British Journal of Radiology, 1993, 66, 522–527.

PROTON Treatment Center Newsletter, vol. 2, No. 4, Oct. 1992, Loma Linda University Medical Center.

Relocatable Frame for Sterotactic External Beam Radiotherapy; Gill et al., Int. J. Radiation Oncology Biol. Phys. vol. 20, pp. 599–603.

Primary Examiner—Stephen C. Pellegrino
Assistant Examiner—Glenn Dawson
Attorney, Agent, or Firm—Knobbe, Martens, Olson & Bear

[57] ABSTRACT

A stereotactic fixation apparatus provides for accurate and reproducible positioning of a patient's skull during medical diagnostic and treatment procedures. The stereotactic fixation apparatus includes a mouthpiece having a bite block formed as an impression of the patient's upper teeth and hard palate. The mouthpiece is connected to a stereotactic frame, which in turn is releasable connected to an adaptor board on which the patient rests. Vacuum pressure is used to draw the bite block firmly against the patient's hard palate. Vacuum pressure is also used to hold the stereotactic frame on the adaptor board. The stereotactic fixation apparatus additionally includes a patient-activated safety release mechanism which allows the patient to disconnect the vacuum pressure and to dislodge the restraints of the mouthpiece and frame, as well as to disable the medical equipment used with the medical diagnostic or treatment procedure.

36 Claims, 8 Drawing Sheets

VACUUM-ASSISTED FIXATION APPARATUS

BACKGROUND OF THE INVENTION

1. Field of the Invention

The present invention relates to an apparatus for immobilizing a patient's skull during a medical diagnostic or treatment procedure, and more particularly to a stereotactic fixation apparatus which permits precise and reproducible positioning of the patient's skull for focal irradiation or like medical procedures.

2. Description of Related Art

Modern methods of imaging, such as computerized tomography and magnetic resonance imaging, enable radiation oncologist to precisely delineate volumes of diseased tissue and normal anatomical structures. The data from imaging scans makes it possible to tailor radiation doses to a particular, identifiable treatment volume.

Focal radiation treatment usually involves the use of external beams, such as, for example, photon or proton beams. Such treatment requires accurate positioning and immobilization of the patient because a small misalignment in a patient's position with respect to the external beam can result in missing the target and/or delivering the high dose of radiation to normal, non-targeted tissue. The distance from the high-dose region of the external beam to its lateral and distal edges is often but millimeters.

Radiation treatment and pretreatment diagnostic studies also requires reproducible positioning of the patient. Radiotherapy typically involves several diagnostic, planning and treatment stages. At each stage subsequent to the initial, accurate repositioning of the patient is essential. Most patients also require multiple treatments extending over several weeks. Variation of the treatment position between different sessions will decrease the efficacy of the treatment.

In an effort to provide accurate and reproducible positioning of a patient, stereotactic location devices have been developed. These devices rely on the assumption that the skull and its contents are rigid. Each anatomic point within the skull can then be uniquely identified when one knows the three spacial coordinates of that anatomic point.

Original neurosurgical and radiosurgical stereotactic location devices typically attach to the patient's skull by three or four pins surgically affixed. These invasive devices cannot be removed between diagnostic studies and treatment procedures, which therefore have to be performed within one day.

More recently, a relocatable stereotactic location device has been developed which employs a halo-ring which is invasively attached to the patient's skull and remains in place for several weeks unless the treatment is finished. An example of these devices are described in Clark, B. G., et al., "A Halo-Ring Technique for Fractionated Stereotactic Radiotherapy," *The British Journal of Radiation,* pp. 522–527 (June 1993). Such devices, however, are still invasive and may cause discomfort to the patient.

Another prior relocatable stereotactic device is described in Delannes, M., et al., "The Laitinen Stereoadaptor," *Neurochirurgie,* 1990, 36:167–175. This device can be quickly positioned on the patient's head using two ear plugs and a nasal support to locate the device on the skull. However, because these fixation points contact relatively soft tissue, such device inherently lacks the rigidity and reproducibility of bony or dental fixation.

Another prior stereotactic device has also used the upper teeth or alveolar ridge to position the stereotactic device on the patient's skull. The rigid connection between the upper teeth and the skull make the upper teeth a convenient and non-invasive reference point of the skull. This stereotactic device is disclosed in U.K. Patent Publication 2 213 066. Straps or similar structure are used in these devices to secure a mouthpiece of the stereotactic device within the patient's mouth. These straps, however, are awkward and time consuming to use, and can contribute to misalignment in head position. In addition, such straps cannot be easily and immediately removed in exigent circumstances. For instance, in cases where the patient chokes, vomits, or otherwise has trouble breathing, the mouthpiece cannot be quickly removed either by the health care provider or by the patient. In addition, a health care provider may also not immediately recognize the patient's condition because the stereotactic location device has immobilized the patient's head, and the patient may be unable to alert the health care provider of his or her condition.

Another disadvantage of using straps is that they may be variably located in the radiation treatment field, thus compromising the quality and reproducibility of dose delivery, especially where charged particles, such as protons, are used.

SUMMARY OF THE INVENTION

In view of the foregoing drawbacks and shortcomings of the prior stereotactic location devices, a need exists for a stereotactic location device which is noninvasive, provides sufficient immobilization, allows accurate re-positioning, is well tolerated by a patient, is quickly released and does not interfere with the medical procedure (e.g., interfere with an external beam in radiotherapy).

In accordance with one aspect of the present invention, a stereotactic fixation apparatus comprises a mouthpiece attached to a stereotactic frame. The mouthpiece has a surface that contacts tissue of a patient, particularly the patient's hard palate, and also has a port adapted for connection to a source of vacuum. Additionally, the mouthpiece is configured to provide a fluidic path between the surface and the port. In the preferred embodiment, the surface of the mouthpiece is shaped to conform to the hard palate of the patient and has at least one hole that communicates with the port. A normally closed, one-way flow valve may be positioned in the fluidic path between the hole and the port. Additionally, the apparatus preferably includes a vacuum control system which regulates the vacuum and a patient-activated switch for terminating vacuum pressure in the fluidic path.

A further aspect of the present invention relates to a stereotactic fixation apparatus that comprises a platform for supporting the body of a patient. A stereotactic immobilization device, such as a stereotactic frame, contacts the platform at least at one interface region. A port, connected to a source of vacuum, is in fluidic communication with the interface region. When a vacuum pressure is applied to the interface region through the port, the vacuum holds the stereotactic immobilization device against the platform. Preferably, the above-mentioned patient-actuated switch serves to terminate vacuum pressure not only to the mouthpiece, but also to the stereotactic immobilization device.

According to another aspect of the invention, a method of accurately and reproducibly positioning a patient's skull for a medical procedure involves the use of a mouthpiece attached to a stereotactic frame. The mouthpiece is positioned within the patient's mouth so as to extend beneath the patient's hard palate. A vacuum is applied to draw the mouthpiece against the patient's hard palate so as to secure the mouthpiece within the patient's mouth.

Yet another aspect of the invention comprises a method of manufacturing a mouthpiece for a stereotactic fixation apparatus. A dental impression of a patient's teeth is made using a first material, and a study cast of the patient's teeth is made using the dental impression. An impression of the study cast is then made using a second material different from the first material to provide a bite block. A passageway is formed through the mouthpiece to provide a path for drawing the mouthpiece against the interior of the patient's mouth.

An additional aspect of the invention comprises a coupling that couples a stereotactic frame to a mouthpiece. The coupling is configured to provide at least three degrees of rotational movement of the mouthpiece relative to the stereotactic frame and at least two degrees of linear movement of the mouthpiece relative to the stereotactic frame.

BRIEF DESCRIPTION OF THE DRAWINGS

These and other features of the invention will now be described with reference to the drawings of preferred embodiments which are intended to illustrate and not the limit the invention, and in which.

DETAILED DESCRIPTION OF PREFERRED EMBODIMENTS

Figure 1:
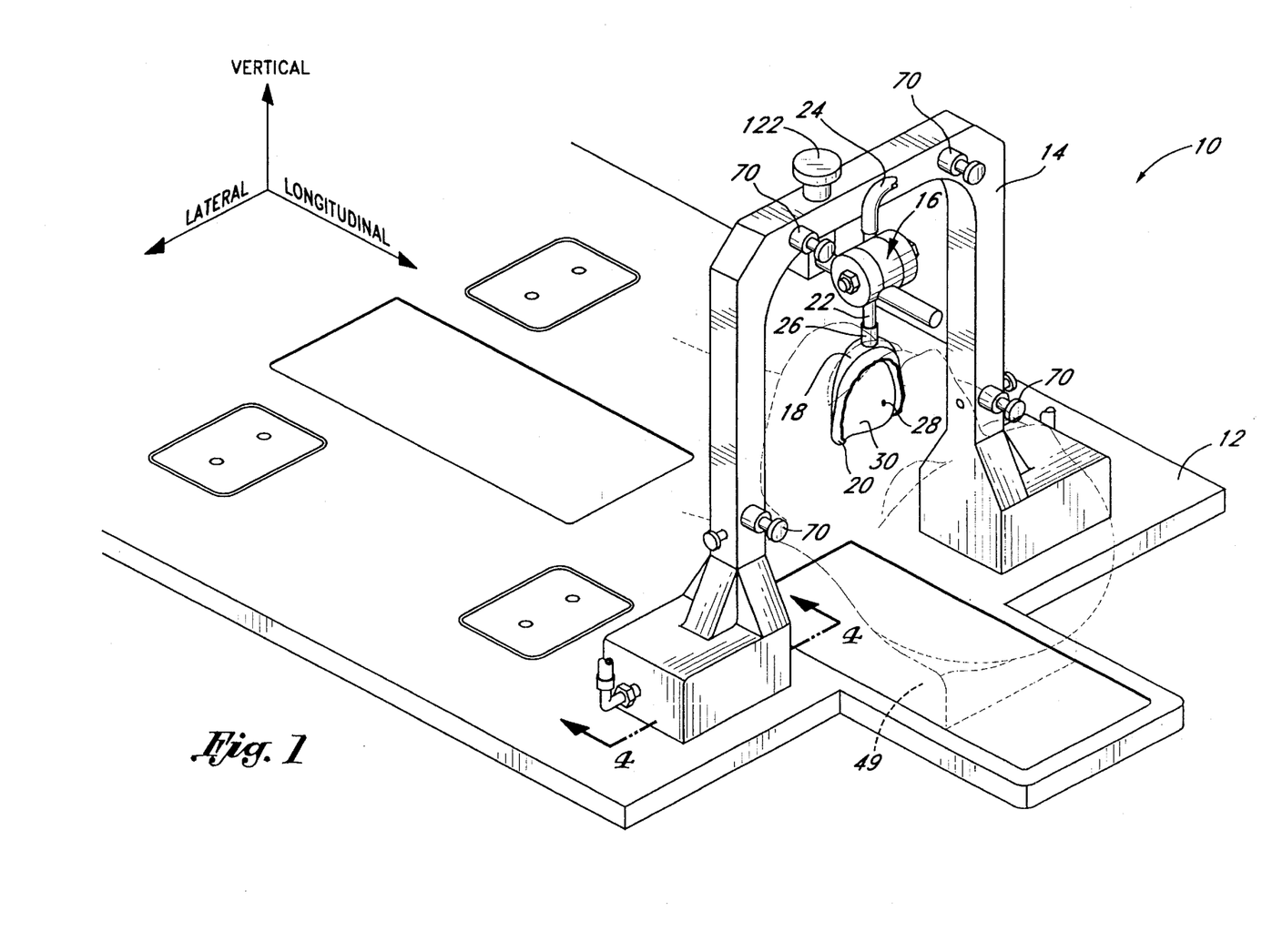
FIG. 1 is a top perspective view a vacuum-assisted stereotactic fixation apparatus in accordance with one preferred embodiment of the present invention.

FIG. 1 illustrates a stereotactic fixation apparatus 10 configured in accordance with a preferred embodiment of the present invention. The stereotactic fixation apparatus 10 is designed to immobilize a patient's skull, and is typically used with focal radiation therapy involving proton beam treatment. It is contemplated, however, that the present stereotactic fixation apparatus can be used in connection with a variety of medical diagnostic and treatment procedures.

With reference to FIG. 1, the stereotactic fixation apparatus 10 principally comprises a generally flat adaptor board or platform 12 supporting a stereotactic frame 14. A vacuum interface is used to secure the frame 14 to the adaptor board 12, as discussed in detail below.

A coupling or universal joint 16 extends outwardly from the frame 14 and supports a mouthpiece 18. The universal joint 16, which connects the mouthpiece 18 to the frame 14, allows a wide range of different positions and orientations of the mouthpiece 18 in relation to the stereotactic frame 14. Once set in a desired position, the universal joint 16 is locked and remains attached to the mouthpiece 18 throughout all subsequent planning and treatment phases of the patient's course. In this manner, the universal joint 16 forms a mechanical memory of the patient's head position with respect to the stereotactic frame 14.

The mouthpiece 18 includes a bite block 20 formed as an impression of the patient's upper mouth. A vacuum is used to removably secure the mouthpiece 18 onto the hard palate and upper teeth of the patient. For this purpose, the mouthpiece 18 connects to a vacuum source via a rigid tube 22, which passes through the universal joint 16 and connects to a flexible vacuum line 24. The mouthpiece 18 is also configured to provide a fluidic path between a port 26 to which the tube is connected and at least one hole 28 in an upper surface 30 of the bite block 20. When used, a vacuum is applied between the mouthpiece 18 and the patient's upper mouth to precisely position and secure the bite block 20 to the patient's dentition and hard palate.

Figure 2:
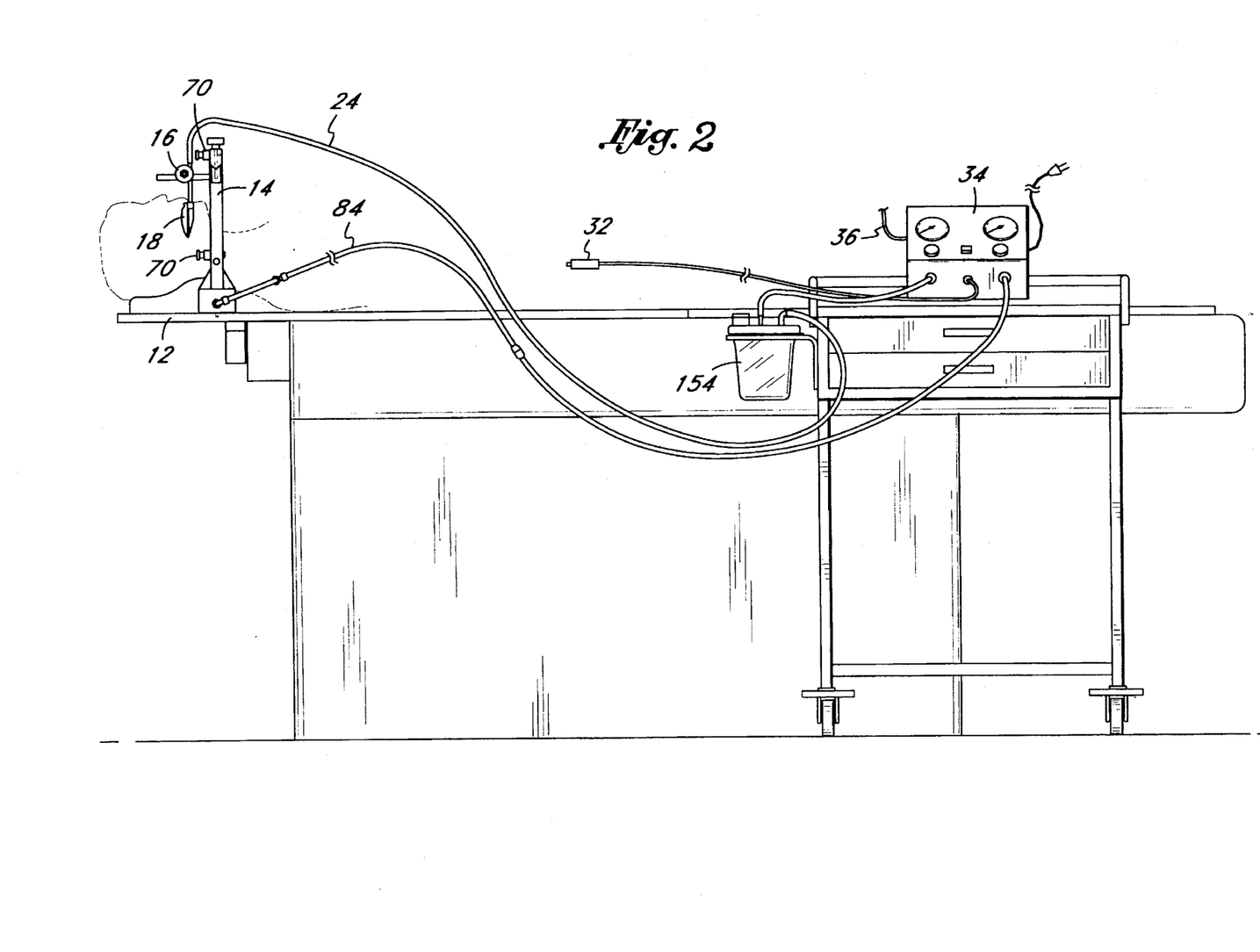
FIG. 2 is a schematic front elevational view of the stereotactic fixation apparatus of FIG. 1.

With reference to FIG. 2, the stereotactic fixation apparatus 10 may also include a patient-activated quick-release mechanism with a safety interlock. This quick-release mechanism includes a patient-activated switch 32 connected to a vacuum control system 34. The vacuum control system 34 controls the application of vacuum pressure to the mouthpiece 18 and to the vacuum interface between the stereotactic frame 14 and the adaptor board 12, as discussed in detail below. When the patient activates the switch 32, the vacuum control system 34 disconnects the vacuum sources from the mouthpiece 18 and the adaptor board 12/stereotactic frame 14 interface so that the patient can dislodge the mouthpiece 18 from his or her mouth, as well as remove the frame 14 from a position surrounding the patient's head.

The vacuum control system 34 also electronically communicates via line 36 with a medical diagnostic or treatment device (not shown), such as, for example, a CAT (computer axial tomography) or MRI (magnetic resonance image) scanner, or an irradiation treatment machine. When the patient activates the switch 32, the control system 34 deactivates the medical diagnostic or treatment apparatus so as not to expose non-target site tissue to any irradiation emitted by the diagnostic or treatment apparatus.

For purposes of describing the preferred embodiment, a coordinate system is provided as illustrated in FIG. 1. Additionally, as used herein, "the longitudinal direction" refers to a direction substantially parallel to the longitudinal axis. "The lateral direction" and "the vertical direction" are likewise in reference to the lateral axis and vertical axis, respectively.

The individual components of the stereotactic fixation apparatus 10 will now be described in detail with reference to FIGS. 1–10.

Adaptor Board

Figure 3:
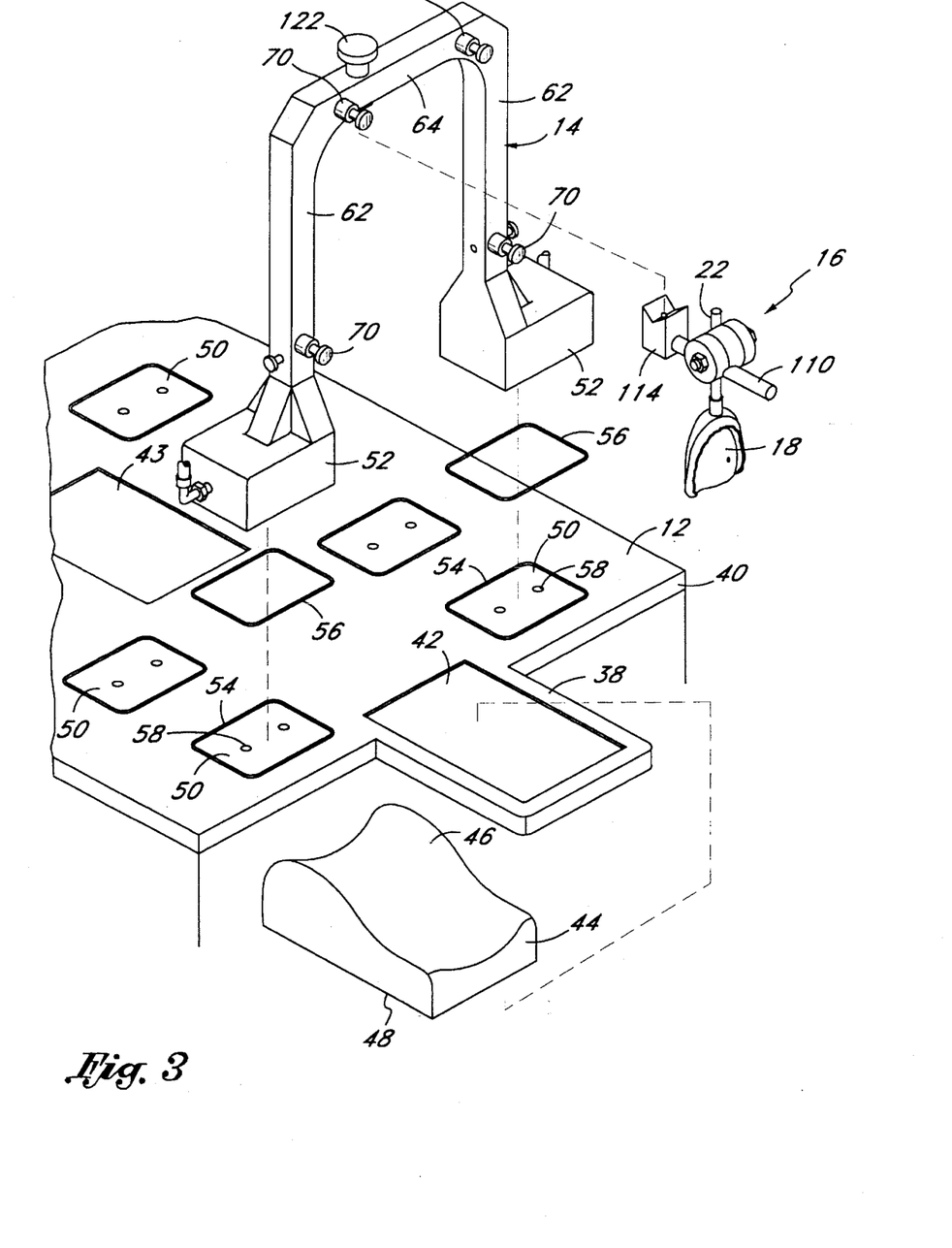
FIG. 3 is an exploded top perspective view of the stereotactic fixation apparatus of FIG. 1.

FIGS. 1–3 best illustrate the adaptor board 12. The adaptor board 12 generally has a rectangular shape sized to support an adult body in a supine position. The adaptor board 12 desirably has a size and shape which is coextensive with conventional gurneys or hospital diagnostic and treatment tables. The adaptor board 12 can thus be placed onto a diagnostic or treatment table or gurney when a medical procedure is preformed using the present stereotactic fixation apparatus 10. It is also contemplated that the adaptor board 12 can alternatively be integrally formed with a dedicated diagnostic or radiation therapy treatment table or gurney.

As illustrated in FIG. 3, the adaptor board 12 may include a rectangular-shaped plank 38 which cantilevers from a superior end 40 of the adaptor board 12. The plank 38 has a width and a length slightly larger than that of a human skull. In an exemplary embodiment, the plank 38 has a length approximately equal to 10 inches (25.4 cm) and a width approximately equal to 8 inches (20.3 cm). It is understood, however, that the plank 38 could have a variety of shapes and sizes, depending upon the specific application of the stereotactic fixation apparatus 10.

The adaptor board 12, proximate to its superior end 40, defines a first rectangular recess 42 positioned generally symmetric with a longitudinal axis of the adaptor board 12. The recess 42 has a length that extends from a point proximate to the superior end 40 into the plank 38. The recess 42 is sized to receive a portion of a headrest 44 (see FIG. 3), which supports the patient's head and neck during the medical procedure.

The adaptor board 12 additionally includes a second rectangular recess 43 also positioned generally symmetrically with the longitudinal axis of the adaptor board 12. The second recess 43 is located below the first recess 42, and has a shape and size substantially identical to those of the first recess 43.

As illustrated in FIG. 3, the headrest 44 used with the adaptor board or platform 12 has an arcuate upper surface 46 which cradles the patient's skull and the nape of the patient's neck. A base 48 of the headrest 44 has a rectangular shape of a width and length generally equal to those of the recesses 42, 43 so as to be snugly received by recesses 42, 43.

The headrest 44 may be formed of any of a wide variety of material of sufficient rigidity and integrity to support the patient's head and neck. In an exemplary embodiment, the headrest 44 is vacuum-formed plastic. However, those skilled in the art will realize that the headrest 44 can be formed of a variety of different materials by a variety of different methods, known or developed in the art.

With reference to FIG. 3, the adaptor board 12 defines a series of paired stations 50 which interface with corresponding footings 52 of the stereotactic frame 14. Each station 50 includes a generally rectangularly shaped groove 54 into which a correspondingly shaped O-ring 56 is seated. The O-ring 56 is advantageously positioned on the adaptor board 12 rather than on the corresponding footing 52 because the O-ring 56 is less likely to fall off or be displaced when positioned on the adaptor board 12. However, it is contemplated that the O-ring could be secured to the frame footing 52.

The O-ring 56 desirably has a diameter larger than the depth of the corresponding groove 54. The O-ring 56 thus extends above the surface of the adaptor board 12 when seated within the groove 54.

The shape and size of each O-ring 56 desirably matches the general shape and size of the stereotactic frame footing 52. More preferably, each O-ring 56 has a corresponding shape that is slightly smaller than the periphery of the footing 52 such that with the footing 52 positioned over the O-ring 56, the entire O-ring 56 is compressed between the adaptor board 12 and the bottom surface of the footing 52.

Figure 4:
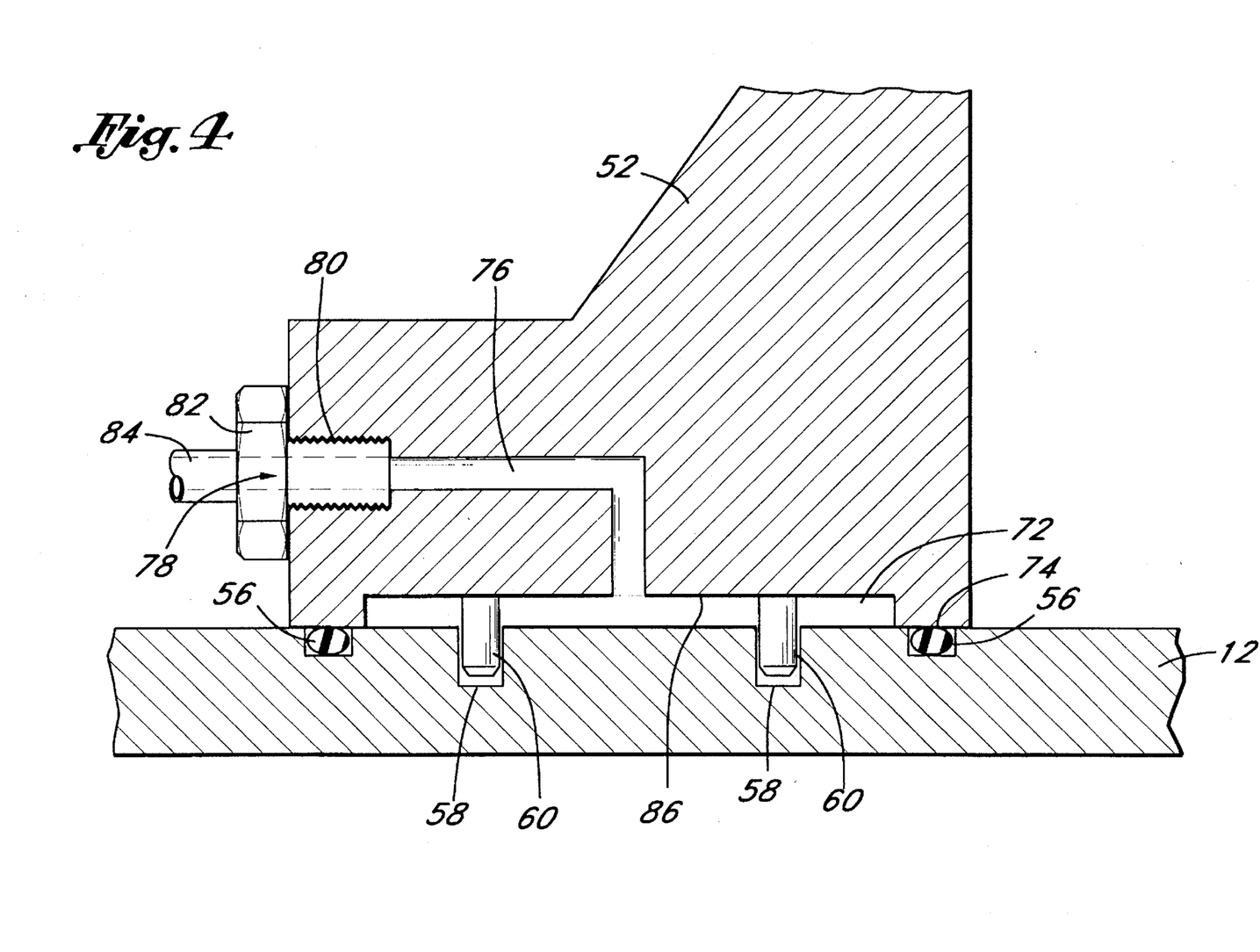
FIG. 4 is a cross-sectional view of a footing of a stereotactic frame taken along line 4—4 of FIG. 1.

With reference to FIG. 4, each station 50 also includes at least two holes 58 sized and positioned to receive guide pins 60 of the corresponding footing 52. These holes 58 are positioned with respect to the O-ring 56 such that with the guide pins 58 inserted into the holes 58, the footing 52 completely covers the O-ring 56. The O-ring 56 thus seals the periphery of the footing 52 at the interface between the footing 52 and the adaptor board 12.

Figure 5A:
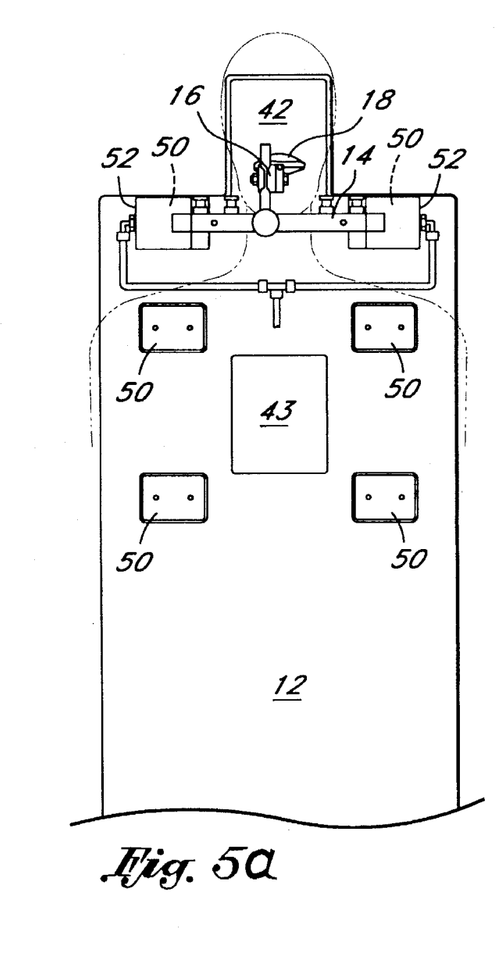
FIG. 5a is a schematic top plan view of the stereotactic fixation apparatus of FIG. 1 with the stereotactic frame in a first treatment position.
Figure 5B:
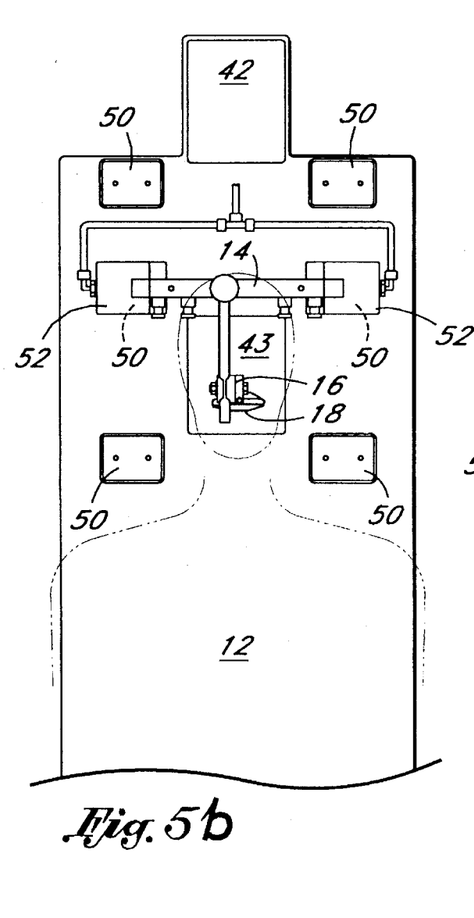
FIG. 5b is a schematic top plan view of the stereotactic fixation apparatus of FIG. 1 with the stereotactic frame in a second treatment position.
Figure 5C:
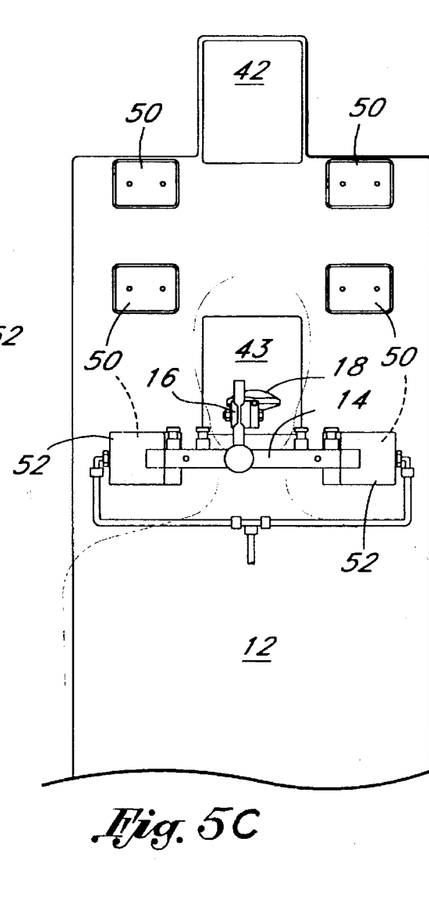
FIG. 5c is a schematic top plan view of the stereotactic fixation apparatus of FIG. 1 with the stereotactic frame in a third treatment position.

FIGS. 5a–5c illustrate the plurality of paired stations 50 of the adaptor table 12. The spacing between these stations 50 is set to position the stereotactic frame 14 either proximate to the patient's shoulders or proximate to the superior portion of the patient's head. The variety of positions of the stereotactic frame 14 on the adaptor board 12 permits the present stereotactic fixation apparatus 10 to be used in radiotherapy procedures where the target is located above the base of the skull or in those procedures where the target is located below the base of the skull.

Stereotactic Frame

With reference to FIG. 3, the stereotactic frame 14 generally has an inverted "U" shape formed by two vertical legs 62 interconnected by an upper horizontal leg 64. The stereotactic frame 14 desirably has a sufficient lateral width and vertical height to surround the skull of the patient.

Each vertical leg 62 terminates in a footing 52. As discussed above, the footings 52 rest flush against the top surface of the adaptor board 12.

Figure 6:
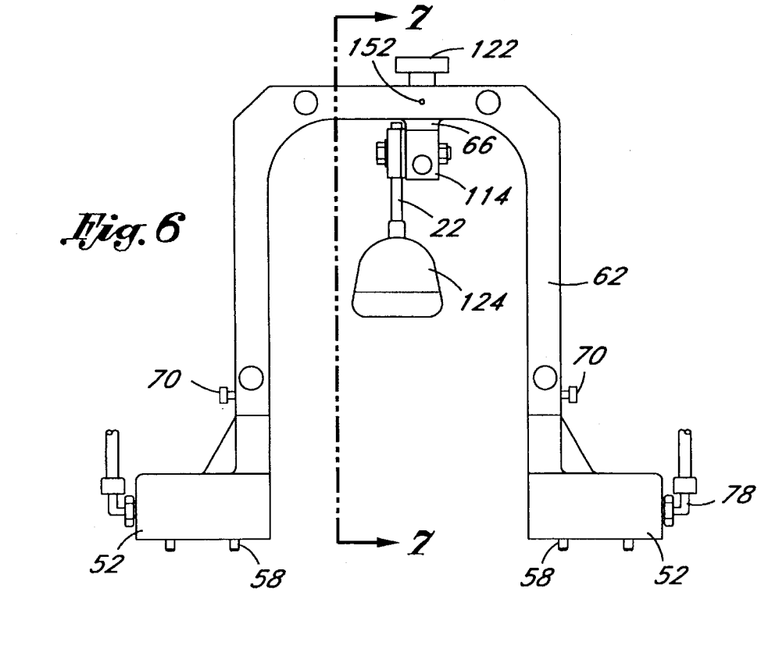
FIG. 6 is a front elevational view of a mouthpiece/ coupling assembly attached to the stereotactic frame of FIG. 1.
Figure 7:
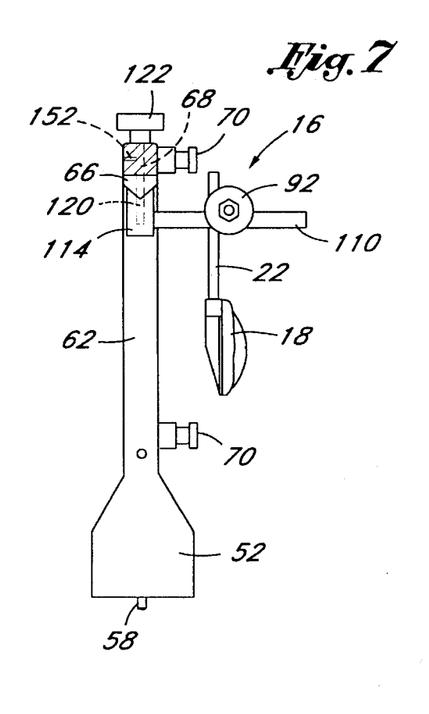
FIG. 7 is a side elevational view of the stereotactic frame and mouthpiece/coupling assembly taken along line 7—7 of FIG. 6.
Figure 8:
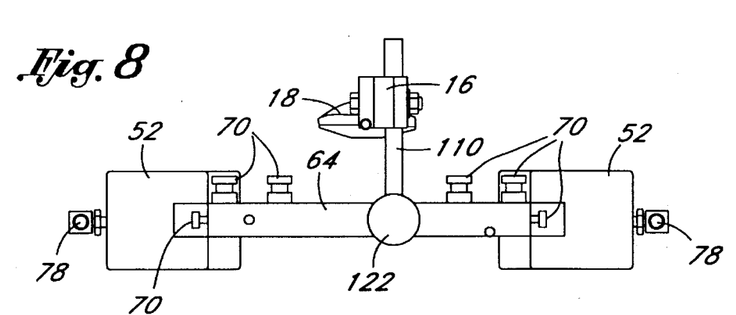
FIG. 8 is a top plan view of the stereotactic frame and mouthpiece/coupling assembly of FIG. 6.

As best seen in FIGS. 6 and 7, the horizontal leg 64 of the stereotactic frame 14 includes a tang 66 to which the universal joint 16 is attached. The tang 66 extends from the horizontal leg 64 toward the adaptor base 12, and, as best seen in FIG. 7, has a "V" shape. With reference to FIG. 6, the tang 66 extends from the horizontal leg 64 at an asymmetric position with respect to the vertical legs 62. This asymmetric position is selected to symmetrically position the mouthpiece 18 between the vertical legs 62 when the coupling 16 is attached to the tang 68, as best seen in FIG. 6.

The horizontal leg 64 also includes a bore 68 that extends in the vertical direction through the horizontal leg 64. An axis of the bore 68 is desirably aligned with the center line of the V-shaped tang 66.

The stereotactic frame 14 also includes a plurality of pins 70 positioned on the vertical and horizontal legs 62, 64. The pins 70 are used to support a stereotactic reference phantom (not shown), which is used to align the stereotactic target with the isocenter of the treatment machine, as discussed more fully in the article "Research in Immobilization and Repeatable Positioning," *Proton Treatment Center Newsletter*, vol. 2, no. 4, Oct. 1992, which is incorporated by reference herein.

With reference to FIG. 4, each footing 52 has a generally rectangular block shape. A recess 72 extends into the footing 52 from a bottom surface 74. The footing 52 also includes a channel 76 that extends from the recess 72 to an effluent port 78, desirably positioned on the outer lateral side of the footing 52. It should be noted, however, that a recess, channel and port could alternatively be formed in the adaptor board 12.

The effluent port 78 is formed by a threaded counterbore 80, which circumscribes the channel 76. A conventional tube fitting 82 is threaded into the threaded bore 80 to complete the port 78.

A vacuum tube 84 is attached to the fitting 82 to interconnect the vacuum tube 84 to the footing 52 and to place the recess 72 in fluidic communication with the vacuum tube 84.

As noted above, each footing 52 includes at least two guide pins 60 that extend downwardly from a bottom surface 86 of the recess 82. The guide pins 60 are advantageously positioned in reference to the periphery of the recess 72 so as to position the recess 72 within the circumference of the O-ring 56 when the guide pins 60 are inserted into the corresponding holes 58 in the adaptor board 12.

Universal Joint

Figure 9:
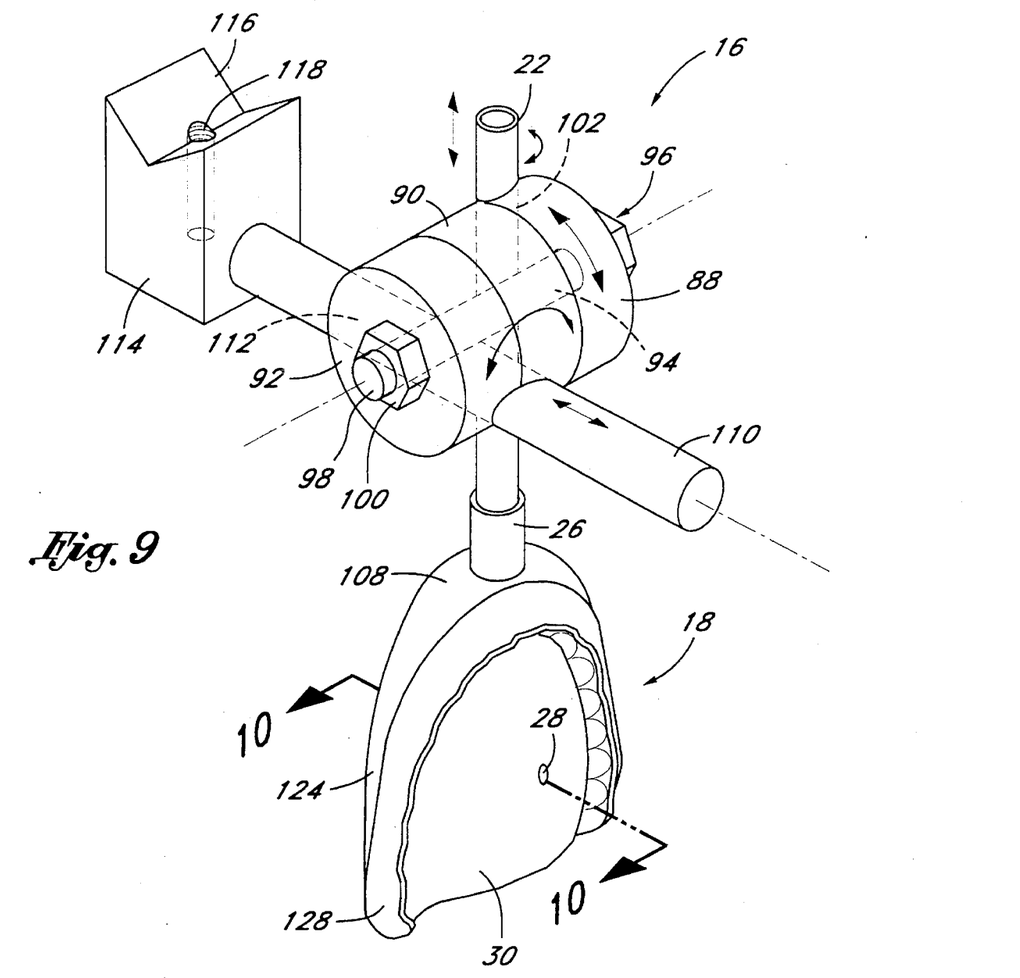
FIG. 9 is an enlarged top perspective view of the mouthpiece/coupling assembly of FIG. 1.

With reference to FIG. 9, the universal joint 16 is desirably formed by a plurality of adjacent discs. In an exemplary embodiment the universal joint 16 includes three adjacent discs 88, 90, 92. The axes of the discs 88, 90, 92 are collinear. A bore 94, concentrically positioned about the axis of the disc 88, 90, 92, extends through the disc assembly.

A fastener 96, such as a nut 98 and bolt 100, is used to join the discs 88, 90, 92 together. The bolt 98 passes through the bore 94. The nut 96 threads onto the bolt 98 from the opposite side to secure the bolt 98 within the bore 94.

The first end disc 88 includes a first bore 102 that passes through the first end disc 88 in a direction generally normal to the axis of the central bore 94. The first bore 102 is also offset from the center of the disc 88 so as not to intersect with the central bore 94. Thus, the first bore 102 extends along an arc length of the first end disc 88, rather than along a diameter of the first end disc 88. So positioned, a small arc length of the first bore 102 is truncated. That is, the first bore 102 breaks through a lateral side surface (not shown) of the disc 88. The corresponding truncated arc length is desirably less than 30°, and more preferably equal to about 10°.

The first bore 102 receives the generally rigid tube 22, which in turn is attached to the mouthpiece 18 via the tube fitting 26 positioned on an anterior end 108 of the mouthpiece 18. The tube 22 has a diameter slightly smaller than that of the first bore 102 so that the tube can be rotated within the bore 102.

With the tube 22 inserted through the first bore 102, a small portion of the tube's external surface extends beyond the flat lateral side surface of the first end disc 88 and lightly contacts the opposing flat lateral surface of the center disc 90. When the fastener 96 is loosened, the tube 22 can rotate relative to the first end disc 88, and the first end disc 88 can rotate relative to the center disc 90. When the fastener 96 is tightened, however, the frictional contact between the first end disc 88 and the center disc 90 prevents the first end disc 88 from rotating relative to the center disc 90. Likewise, the frictional contact between the center disc 90 and the exterior portion of the tube 22 that extends beyond the lateral side surface of the first end disc 88 prevents the tube 22 from rotating within the first bore 102 of the first end disc 88.

The universal joint 16 also includes a mounting rod 110 that extends in the longitudinal direction, normal to the common axis of the disc assembly. The rod 110 extends through a second bore 112. The second bore passes through the central disc 90 and a second end disc 92 at the interface of the central disc 90 and the second end disc 92. The second bore 112 is also offset from the center of the discs 90, 92 so as not to intersect with the central bore 94. Thus, the second bore 112 extends along an arc length of the discs 90, 92, rather than along a diameter of the discs 90, 92.

The rod 110 is inserted through the second bore 112 and is captured between the center disc 90 and the second end disc 92. This configuration allows the universal joint 16 to be rotated about the rod 110 when the fastener 96 is loosened. When the fastener 96 is tightened, the central disc 90 and the second end disc 92 clamp against the rod 110 to prevent rotation of the disc assembly about the rod 110.

With reference to FIG. 9, one end of the support rod 110 connects to a mount block 114. The mount block 114 has a generally rectangular block-like shape with a V-shaped notch 116 formed on an upper end. The shape of the V-notch 116 desirably matches that of the V-shaped tang 66 on the stereotactic frame 14. The mount block 114 also includes a threaded bore 118 that extends in the vertical direction through the block 114. The axis of the bore 118 substantially coincides with a center line of the block 114 in the vertical direction.

As discussed below, the mounting block 114 is attached to the horizontal leg 64 of the stereotactic frame 14, and is positioned thereon by inserting the V-shaped tang 66 into the correspondingly V-shaped notch 116 of the mount block 114. With reference to FIG. 7, an elongated threaded shaft 120 of the knob 122 is inserted through the bore 68 and engages the threaded bore 118 of the mount block 114. In this manner, the universal joint 16 is secured to the stereotactic frame 14.

Mouthpiece

Figure 10:
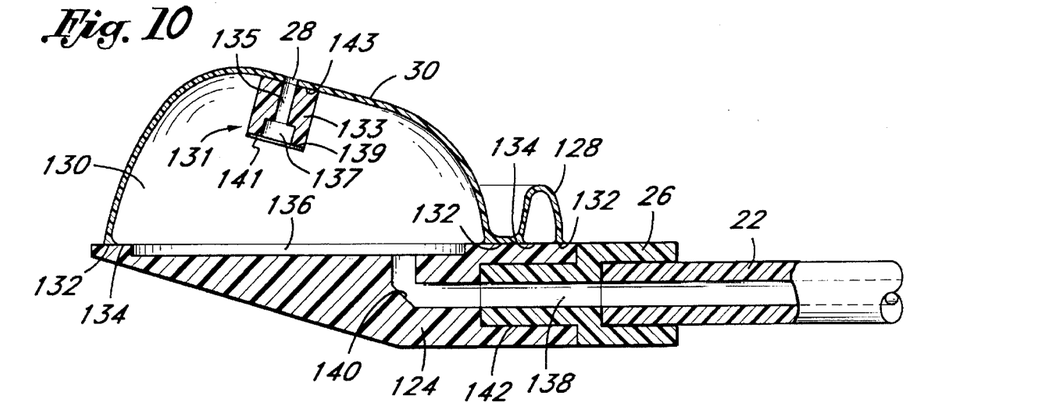
FIG. 10 is a cross-sectional view of the mouthpiece taken along line 10—10 of FIG. 9.

With reference to FIGS. 9 and 10, the mouthpiece 18 includes the bite block 20 attached to a bite block tray 124. The mouthpiece 18 generally has a U-shape that corresponds to the shape of the patient's upper dentition.

FIG. 10 illustrates a cross section of the mouthpiece 18. The bite block 20 has an upper surface 30 that is, as noted above, a reproduction of an impression of the patient's dentition and hard palate. The bite block 20 includes a skirt 128, which extends upwardly and surrounds the circumference of the U-shaped bite block 20 so as to extend over the outer surfaces of the patient's upper teeth when inserted in the patient's mouth.

A hollow 130 is formed inside the bite block 20. The aperture 28 is formed between the inner surface of the hollow 30 and the upper surface 30 of the bite block 20. The aperture 28 places the hollow 130 in fluidic communication with the upper surface 30 of the bite block 20. A flat bottom surface 132 circumscribes the hollow 130, as well as extends around the periphery of the bite block 20.

The bite block 20 is formed by first taking an impression of the patient's dentition and upper palate. A putty-like material, such as, for example, alginate or silicon, is spread into a conventional dental tray. The dental tray is then placed in the patient's mouth and is pushed upwardly against the upper teeth and hard palate to take an impression. The material desirably hardens within a short period of time (e.g., 90 seconds). The hardened impression is then removed from the patient's mouth.

A study cast is made of the patient's dentition and hard palate using the dental impression. A study cast, as known in the art, is a permanent, exact reproduction of the patient's upper dentition and roof of mouth.

The cast, in turn, becomes the basis for the bite block itself. The bite block 20 is formed by sputtering a layer of self-curing orthodontic resin over the study cast. This process is repeated several times until the bite block 20 has a desired thickness. The bite block advantageously has a sufficient thickness to provide the necessary structural integrity such that the bite block does not crack or break during use. In an exemplary embodiment, the bite block 20 has a thickness equal to about ⅛ inch (0.3 cm). It is contemplated, however, that the bite block 20 can have a thickness of any of a variety of sizes depending upon the particular application of the bite block 20. The bite block 20 is then attached to the dental tray 124 using a moldable orthodontic resin, such as TRIAD®-VLC resin, which is cured with visible light.

With the bite block 20 attached to the study cast, the sealing skirt 128 is put around the circumference of the bite block 20 and molded to the outer surface of the upper teeth. A visible light-cured soft denture reline, such as Lite Line®-VLC, is preferably used to form the seal 120. In addition, the distal margin of the bite block surface 30 may be sealed, for example, using a medical adhesive, such as Rehau® raumedic adhesive SI 1511.

Formed from the study cast, the bite block 20 reproduces the impression, not only of the patient's teeth (or alveolar ridge, if the patient is edentulous) but also the entire surface of the hard palate.

The hole 28 is then placed in the upper surface 30 of the bite block 20 to form a passageway from the upper surface 30 into the hollow 130 inside the bite block 20.

A normally closed, one-directional flow valve 131 may be used with the bite block 20 as an added safeguard to prevent the patent from dislodging the mouthpiece 18. With reference to FIG. 10, the valve 131 includes a valve body 133 having a tubular shape with a central channel 135 passing therethrough. The channel 135 of the valve 131 desirably has a diameter matching that of the hole 28 in the bite block upper surface 30.

A counterbore 137 extends into the valve body 133 from a lower end 139, and is desirably concentric with the central channel 135. The valve 131 further includes a valve flap 141 formed of an elastic material with sufficient structural integrity to remain normally closed, yet open slightly when the pressure in the hollow 130 of the bite block 20 is less than the pressure in the counterbore 137. The elastic material preferably comprises a silicon sheet; however, it is understood that any of a wide variety of materials may be used as well. About three-quarters of the circumference of the valve flap 141 is glued onto a corresponding portion of the valve body periphery at the lower end 139.

A second end 143 of the valve is attached to the inner surface of the hollow 130 of the bite block 20 by an epoxy adhesive. Desirably, the hole 28 in the upper surface 30 of the bite block 20 and the channel 135 of the valve 131 are aligned.

The volume within the valve body 133 desirably is substantially less (e.g., 10% or less) than the volume within the hollow 130 of the bite block 20.

As illustrated in FIG. 10, the bite block tray 124 includes a generally flat platform 134 having a size and shape generally coextensive with that of the bite block bottom surface 132. The platform 134 includes a recess 136 positioned within the circumferential edges of the platform 134.

As best seen in FIG. 7, the bite block tray 124 desirably has a minimal profile to minimize the invasiveness of the bite block tray 124 when inserted in the patient's mouth. In the exemplary embodiment, the maximum thickness of the bite block tray 124 is about 0.5 inch (1.3 cm); however, those skilled in the art will readily appreciate that the bite block tray 124 could be formed of a wide variety of sizes, depending upon the specific application of the mouthpiece 18. In an exemplary embodiment, as illustrated in FIG. 10, the bite block tray 124 has a generally triangular cross-sectional shape. This shape reduces the obtrusiveness of the mouthpiece 18 when worn by the patient, as the width of the mouthpiece 18 is reduced towards the back of the patient's palate so as to fit more comfortably within the patient's mouth.

FIG. 10 illustrates an internal channel 138 formed between the anterior end 108 of the bite block tray 124 and the platform recess 136. The channel 138 preferably has a circular cross-sectional shape equal to that of the inner lumen of the tube 22. The channel 138 extends normal to both the platform surface 134 and to the anterior end 108 of the bite block tray 124 and includes a 90° bend between these two sections of the channel 138. The wall of the channel 138 may include a chamfer 140 at the 90° bend to improve fluidic flow through the channel 138, as known in the art.

The anterior end 108 of the bite block tray 124 also includes a counterbore 142 that circumscribes the channel 138. The counterbore 142, as illustrated in FIG. 10, receives the conventional tube fitting 26 to attach the tube 22 to the bite block tray 124, with the inner lumen of the tube 22 communicating with the channel 138 of the bite block tray 124. The fitting 26 desirably has a diameter substantially equal to or less than the width of the bite block tray 124 at its anterior end 108 such that the fitting 26 sits flush against the anterior end 108 of the bite block tray 124.

When the bite block 20 is mounted to the tray 124, a fluidic path is formed from the port 26 of the tray 124, through the channel 138, into the hollow 130 of the bite block 20, and through the hole 28 in the upper surface 30 of the bite block 20.

Patient-Activated Quick-Release Mechanism

As discussed above, the stereotactic fixation apparatus 10 may also include a patient-activated quick-release mechanism. With reference to FIG. 2, the patient-activated switch 32 communicates with the vacuum control system 34. The vacuum control system 34 controls the application of vacuum pressure to the mouthpiece 18 and to the interface region between the stereotactic frame 14 and adaptor board 12. In an exemplary embodiment, the vacuum control system includes at least two solenoid valves which are positioned between the vacuum source and the ports 78, 26 of the stereotactic frame footings 52 and the mouthpiece 18, respectively. When the stereotactic frame 14 is attached to a patient's skull, the vacuum control system 34 holds the solenoid valves open such that a vacuum is drawn in the mouthpiece 18 and at the interface between the stereotactic frame 14 and the adaptor board 12. In this manner, the mouthpiece 18 is drawn against the patient's hard palate, and the vacuum created between the footings 52 of the stereotactic frame 14 and the adaptor board 12 holds the stereotactic frame 14 against the adaptor board 12.

If the patient activates the switch 32, the vacuum control system 34 closes the solenoid valves to disconnect the vacuum source from the footings 52 of the stereotactic frame 14 and from the mouthpiece 18. The patient may then dislodge the mouthpiece 18 from his or her mouth and remove the frame 14 from the position surrounding the patient's head. In this manner, the patient can quickly remove the stereotactic frame and mouthpiece if the patient chokes, vomits, or otherwise experiences trouble breathing.

As discussed above, the vacuum control system 34 also communicates with the medical diagnostic or treatment device (not shown) used in conjunction with the stereotactic fixation apparatus 10. The vacuum control system 34 communicates with the medical device via line 36, which carries an enable signal to the medical device. When the patient activates the switch 32, the control system 34 interrupts the enable signal to disable the medical device. Any radiation emitted by the medical device immediately ceases so as not to expose non-targeted tissue to irradiation. Thus, the patient can dislodge and remove the restraints of the mouthpiece and stereotactic frame without the danger of unintentional irradiation.

Method of Use

When using the stereotactic fixation apparatus 10, a patient lies on the adaptor board 12 in a supine position. The headrest 44 is placed within the recess 42 or 43 on the board 12, and the patient is positioned such that the headrest 44 cradles the posterior side of the patient's skull and supports the nape of the patient's neck.

The stereotactic frame 14 is then placed over the patient and is positioned at a desired location relative to the patient's skull. Specifically, the guide pins 60 of the stereotactic frame 14 are inserted into the hole 58 of the adaptor board 12 at the desired location. The footings 52 of the stereotactic frame 14 sit on top of the adaptor board 12 and compress the O-rings 56 to seal the cavities formed by the recesses 72 of the footings 52 and the top surface of the adaptor board 12. A vacuum supply line 84 (FIG. 2) is connected to the fitting 82 of each footing 52. A vacuum source is then activated to produce a vacuum within the cavity so as to draw the footing 52 against the adaptor board 12. In this manner, the stereotactic frame 14 is removably secured to the adaptor board 12.

The universal joint 16 is attached to the stereotactic frame 14 by inserting the V-shaped groove 116 of the mount block 114 over the V-shaped tang 66 that extends below the horizontal leg 64 of the stereotactic frame 14. When the surfaces of the tang 66 and groove 116 are in contact, the knob 122 is turned to screw the rod 124 attached to the knob 122 into the threaded bore 118 of the mount block 114. The knob 122 is tightened until the mount block 114 is drawn tightly against the tang 66. A set screw or like locking mechanism inserted through an aperture 152 (see FIGS. 6 and 7) in the horizontal leg 64 of the stereotactic frame 14 may be used to lock the rod 124 in place while the mount block 114 is aligned to the tang 66.

As noted above, the universal joint 16 provides the mouthpiece 18 with three degrees rotational freedom in relation to the stereotactic frame 14. The longitudinal distance between the mouthpiece 18 and the stereotactic frame 14 can also be adjusted by sliding the universal joint 16 along the rod 110. The vertical position of the mouthpiece 18 relative to the stereotactic frame 14 can also be adjusted by sliding the rigid tube 22 through the first bore 102 in the desired direction. In this manner, the mouthpiece 18 can be adjusted relative to the frame 14 during the stereotactic localization procedure.

A vacuum is then applied to the mouthpiece 18 through the port 26 via line 24. The vacuum line 24 is preferably connected to a suction canister 154 (see FIG. 2) which receives any saliva drawn from the patient's mouth, as known in the art.

Vacuum pressure is thus applied to the hard palate through the hole 28 in the upper surface 30 of the bite block 20. The vacuum holds the bite block 20 firmly against the patient's palate and causes the bite block 20 to precisely locate against the patient's dentition and palate.

The highly accurate dental-palatal reproduction and the vacuum thus emplaces and secures the bite block 20 in the same position in the patient's mouth for each diagnostic procedure and subsequent treatments. Because the skull is rigidly connected to the upper dentition and alveolar ridge, the repeatable positioning of the bite block 20 enables one to repeatedly position the patient's head.

As noted above, the present stereotactic fixation apparatus includes a quick release mechanism which enables the patient to quickly dislodge the restraint of the stereotactic frame 14 and mouthpiece 18 in exigent circumstances (e.g., choking, vomiting, etc.). The patient simply presses the switch 32 in such exigent circumstances and sits upright. The patient can then dislodge the mouthpiece 18 from his or her mouth. As discussed above, the vacuum control system 34 disconnects the source of vacuum from the mouthpiece port 26 and the ports 76 of the stereotactic frame 14. The patient can then overcome the residual vacuum pressure by normal movement.

Additional Embodiment

Figure 11:
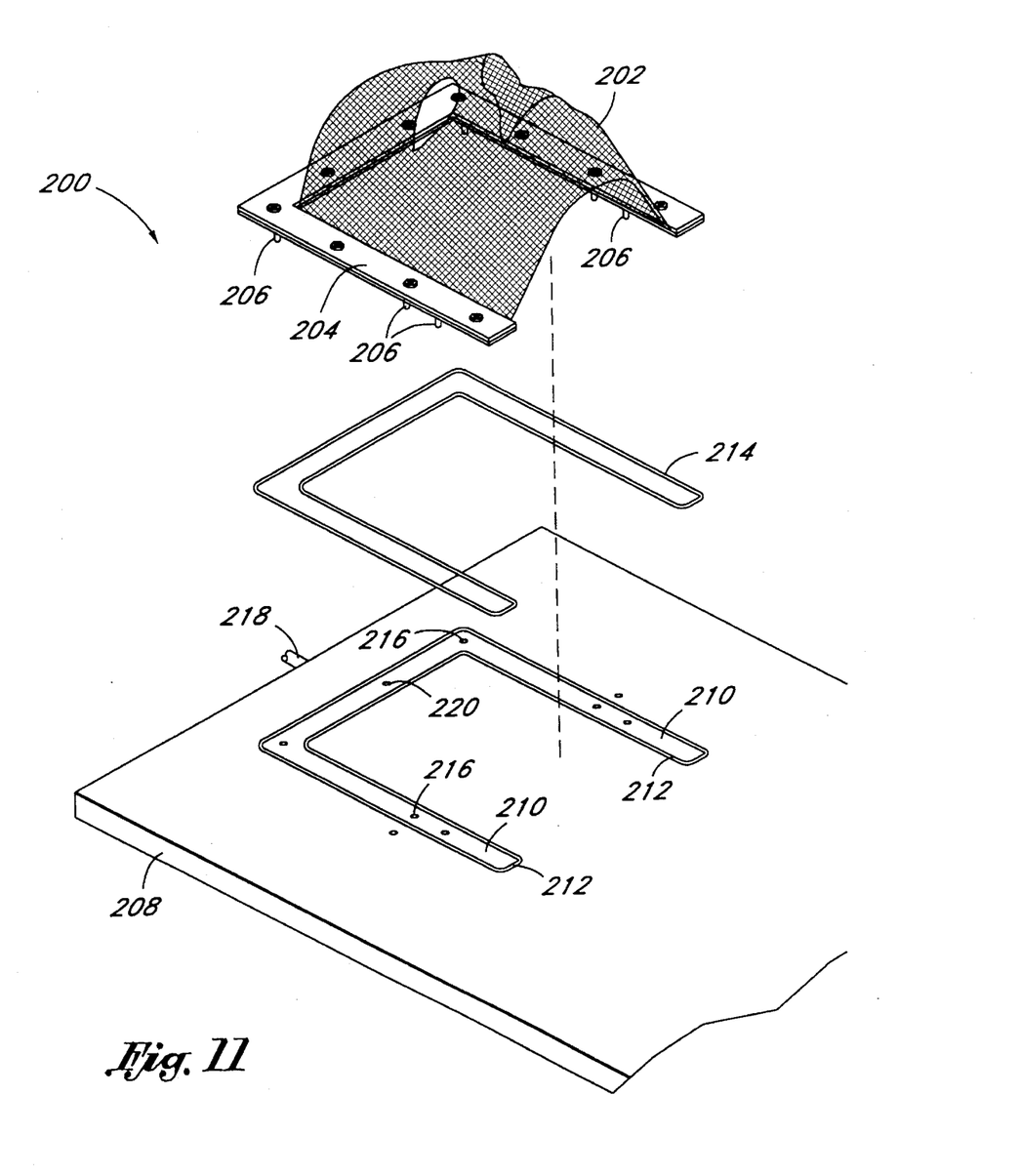
FIG. 11 is an exploded top perspective view of a stereotactic fixation apparatus in accordance with a second preferred embodiment of the present invention.

With reference to FIG. 11, there is provided an additional fixation apparatus 200 configured in accordance with another preferred embodiment of the present invention. The fixation apparatus 200 includes a facial mask 202 formed of a thermoplastic material. The thermoplastic material is heated to a degree in which the material is pliable, and is then placed over the anterior portion of the patient's skull. The material is molded to the contours of the patient's anterior features and is allowed to harden in this configuration. In this manner, the facial mask 202 forms an impression of the patient's facial features.

The facial mask 202 is attached to a mounting frame 204 by conventional means. The mounting frame generally has a U-shape of a sufficient size to surround the periphery of a patient's head. The mounting frame 204 also includes guide pins 206 which are used to position the mounting frame 204, as discussed below.

The fixation apparatus 200 also includes an adaptor board 208. The adaptor board 208 generally has a rectangular shape sized to support an adult body in a supine position. The adaptor board 208 includes a U-shaped recess 210 and a groove 210 that outlines the periphery of the recess 210. The groove 212 and recess 210 are sized smaller than the mounting frame 204 such that the mounting frame 204 completely covers the groove 212 and recess 210.

The adaptor board 208 further includes a seal 214 having a circular cross-sectional shape and configured to sit within the groove 212. The seal 214 desirably has a diameter larger than the depth of the corresponding groove 212, such that the seal 214 extends above the surface of the adaptor board 208 when seated within the groove 212.

The adaptor board 208 further includes alignment holes 216 which cooperate with the guide pins 206 on the mounting frame 204. The alignment holes 216 are positioned with respect to the recess 210 and the groove 212 so as to position the mounting frame 204 over the seal 214 and the recess 210. In this manner, a substantially sealed cavity is formed between the mounting frame 204 and adaptor board 208 when the mounting frame 204 covers the recess 210.

The adaptor board 208 also includes a port 218 connected to a channel (not shown) which extends through the adaptor board 208 and opens into the recess 210 through an aperture 220. The port 218 is adapted to connect to a source of vacuum.

When the fixation apparatus 200 is used in radiotherapy or like medical procedures, the patient is placed on the adaptor board 208 in the supine position. The face mask 202 is then placed over the patient, and the patient's skull is oriented within the face mask 202 such that the face mask 202 sits directly against the anterior features of the patient's skull. The guide pins 206 of the mounting frame 204 are then inserted into the alignment holes 216 of the adaptor board 208 to properly position the mounting frame 204 over the recess 210. The port 218 in the adaptor board 208 is then connected to a vacuum source so as to apply vacuum pressure within the recess 210. The vacuum holds the mounting frame 204 against the adaptor board 208.

The fixation apparatus 200 may also include the patient-activated quick release mechanism discussed above. This quick-release mechanism allows the patient to disconnect the port 218 from the source of vacuum upon activation of the switch 34 (FIG. 2). When the vacuum is disconnected from the port 218, the patient can remove the mounting frame 204 from the adaptor board 208. It should be noted that the vacuum system will inherently have slight leaks such that a vacuum lock is not formed between the mounting frame 204 and the adaptor board 208. Thus, the patient will be able to overcome any residual vacuum pressure by lifting his or her head off of the adaptor board 208.

Although this invention has been described in terms of certain preferred embodiments, other embodiments apparent to those of ordinary skill in the art are also within the scope of this invention. Accordingly, the scope of the invention is intended to be defined only by the claims which follow.

What is claimed is:

1. A stereotactic fixation apparatus, comprising:

a stereotactic frame; and a mouthpiece attached to said stereotactic frame, said mouthpiece having a surface for contacting a patient's hard palate and a port positioned at a point on said mouthpiece distal of said surface and adapted for connection to a source of vacuum, said mouthpiece being configured to provide a fluidic path between said surface and said port to provide a vacuum attachment between the surface and the hard palate of the patient.

2. The stereotactic fixation apparatus of claim 1 additionally comprising a vacuum control system configured to communicate with the source of vacuum so as to regulate vacuum from said source of vacuum and a remote patient-activated switch which communicates with said vacuum control system for terminating vacuum pressure in the fluidic path defined by said mouthpiece.

3. The stereotactic fixation apparatus of claim 1, wherein said surface is shaped to conform to the hard palate of the patient.

4. The stereotactic fixation apparatus of claim 3, additionally comprising a normally closed, one-directional flow valve in communication with the fluidic path provided between said surface and said port of said mouthpiece.

5. The stereotactic fixation apparatus of claim 4, wherein said surface has at least one hole which communicates with said port, said normally closed, one-directional flow valve being in said fluidic path between said hole in said surface and said port.

6. The stereotactic fixation apparatus of claim 5, wherein said hole in said surface opens into a normally sealed cavity formed within said valve, said cavity having a volume significantly less than the volume of said fluidic path of said mouthpiece.

7. The stereotactic fixation apparatus of claim 1 additionally comprising a coupling which connects said mouthpiece to said stereotactic frame, said coupling configured to provide at least three degrees of rotational movement of said mouthpiece relative to said stereotactic frame, and at least two degrees of linear movement of said mouthpiece relative to said stereotactic frame.

8. The stereotactic fixation apparatus of claim 7, wherein said coupling is removably attached to said stereotactic frame.

9. The stereotactic fixation apparatus of claim 7, wherein said coupling includes a locking mechanism which prevents said mouthpiece from moving in reference to said stereotactic frame and which permits said mouthpiece to be repositioned in exactly the same manner to said stereotactic frame.

10. The stereotactic fixation apparatus of claim 9, wherein said coupling comprises:

a plurality of discs having a central bore formed through the center of the discs along a common axis, a first of said discs having a first bore positioned generally normal to said central bore and being positioned in said first disc so as not to intersect with said central bore, a second of said discs having at least a portion of a second bore positioned generally normal to said central bore and being positioned in said second disc so as not to intersect with said central bore;

a fastener having a shaft which passes through said central bore to join said discs together, said fastener having a first unlocked position in which said first and second discs are rotatable about said fastener shaft, and a second locked position in which said first and second discs are nonrotatable about said fastener shaft;

a substantially rigid member extending through said first bore of said first disc, said member and said first disc being adapted to permit said member to rotate about a vertical axis of said member when said fastener is in said unlocked position, and to prevent said member from rotating about said vertical axis of said member when said fastener is in said locked position, said member being connected to said port of said mouthpiece; and a rod adapted to attach to said stereotactic frame, said rod extending through said second bore of said second disc, said rod and said second disc being adapted to permit said second disc to rotate about a longitudinal axis of said rod when said fastener is in said unlocked position, and to prevent said second disc from rotating about said longitudinal axis of said rod when said fastener is in said locked position.

11. The stereotactic fixation apparatus of claim 10, wherein said first bore breaks through a flat lateral surface of said first disc to an extent that no more than an arc length of 30° of an exterior surface of said rigid member extends beyond said flat lateral surface of said first disc with said rigid member extending through said first bore.

12. The stereotactic fixation apparatus of claim 10, wherein said second bore passes through an interface between said second disc and a third disc, a portion of said second bore extending into said third disc.

13. The stereotactic fixation apparatus of claim 10, wherein said rigid member is connected to a source of vacuum.

14. The stereotactic fixation apparatus of claim 1, wherein said mouthpiece comprises an impression of the patient's upper teeth and hard palate.

15. The stereotactic fixation apparatus of claim 14, wherein said mouthpiece additionally comprises a tray onto which said impression is mounted.

16. The stereotactic fixation apparatus of claim 1 additionally comprising a vacuum control system having a remote patient-activated switch which is configured to be held by a patient and which communicates with and controls a valve that is positioned in fluidic communication with said mouthpiece.

17. A fixation apparatus, comprising:
  a platform for supporting a body of a patient;
  a skull immobilization device contacting said platform at least at one interface region; and
  a port adapted for connection to a source of vacuum, said port being in fluidic communication with said interface region and formed in said platform or in said skull immobilization device whereby a vacuum holds said immobilization device against said platform when vacuum pressure is applied to said interface region through said port.

18. The fixation apparatus of claim 17, wherein said immobilization device comprises a stereotactic frame.

19. The fixation apparatus of claim 18, wherein said stereotactic frame has at least two footings which contact said platform at two interface regions, each of said interface regions including a cavity that is in fluidic communication with said port.

20. The fixation apparatus of claim 19, wherein at least one of said cavities is formed in one of said footings 21. The fixation apparatus of claim 19, wherein said at least one of said cavities is formed in said platform.

22. The fixation apparatus of claim 19, further comprising at each of said interface regions an O-ring compressed between said platform and each corresponding footing for forming a seal around each of said cavities.

23. The fixation apparatus of claim 22, wherein at least one of said O-rings is seated in a groove formed in said platform.

24. The fixation apparatus of claim 23 additionally comprising means for positioning at least one of said footings, on said platform such that said corresponding O-ring surrounds the periphery of said corresponding cavity.

25. The fixation apparatus of claim 17 additionally comprising a vacuum control system for communicating with at least the source of vacuum which communicates with at least said port so as to enable or disable the source of vacuum applied to said port, said vacuum control system having a remote patient-activated switch which is configured to be held by said patient and which communicates with said vacuum control system such that said vacuum control system disables the application of vacuum at said port when said patient activates said switch.

26. The fixation apparatus of claim 25, wherein said vacuum control system includes a solenoid valve configured to be positioned between and in fluidic communication with the source of vacuum and said port, said vacuum control system operating said valve in response to said patient-activated switch.

27. The fixation apparatus of claim 17, wherein said stereotactic immobilization device comprises a rigid face mask mounted to a frame, said face mask adapted to have shape which conforms to the contours of the anterior features of the patient's skull.

28. The fixation apparatus of claim 27, wherein said interface region comprises a cavity.

29. The fixation apparatus of claim 28, wherein said cavity is formed in said platform.

30. A method of accurately and reproducibly positioning a patient's skull for a medical procedure, said method comprising the steps of:
  providing a mouthpiece attached to a stereotactic frame;
  positioning said mouthpiece within said patient's mouth in a position in which said mouthpiece extends beneath the patient's hard palate; and
  applying a vacuum to draw said mouthpiece against the patient's hard palate so as to secure said mouthpiece within the patient's mouth.

31. The method of claim 30 additionally comprising the steps of:
  making an impression of the patient's upper teeth and hard palate; and
  mounting said impression on a tray to form said mouthpiece.

32. The method of claim 31, wherein said step of applying a vacuum comprises drawing a vacuum between said impression and the patient's hard palate so as to draw said impression firmly against the patient's hard palate.

33. The method of claim 30 additionally comprising the steps of:
  providing a coupling between said mouthpiece and said stereotactic frame, said coupling providing three degrees of rotational freedom and two degrees of axial freedom in of to said mouthpiece relative to said stereotactic frame;
  adjusting the position of the patient's head to a set position with said mouthpiece secured within the patient's mouth; and
  locking said coupling with said mouthpiece in said set position to prevent the coupling from rotating or moving axially in reference to said stereotactic frame.

34. The method of claim 33 additionally comprising the step of removing said coupling from said stereotactic frame with said mouthpiece remaining attached to said coupling.

35. The method defined in claim 30, wherein said step of providing a mouthpiece comprises:
  making a dental impression of a patient's teeth using a first material;
  making a study cast of said patient's teeth using said dental impression;
  making an impression of said study cast using a second material different from said first material to provide a bite block; and
  forming a passageway through said mouthpiece to provide a path for drawing said mouthpiece against the interior of the patient's mouth.

36. The method defined in claim 35 additionally comprising the step of providing a normally closed, one-directional flow valve in fluidic communication with said passageway.

* * * * *

UNITED STATES PATENT AND TRADEMARK OFFICE
CERTIFICATE OF CORRECTION

PATENT NO. : 5,464,411
DATED : November 7, 1995
INVENTOR(S) : Schulte et al.

It is certified that error appears in the above-indentified patent and that said Letters Patent is hereby corrected as shown below:

```
Column 15, Line 42 change "wherein said at least" to --wherein at
     least--
Column 16, Lines 6-7 change "to have shape" to --to have a shape--
Column 16, Line 38 change "freedom in of to said mouthpiece" to --
     freedom of said mouthpiece--
```

Signed and Sealed this

Twenty-fifth Day of June, 1996

Attest:

BRUCE LEHMAN

Attesting Officer

Commissioner of Patents and Trademarks